United States Patent
Yonezawa

(10) Patent No.: US 9,451,878 B2
(45) Date of Patent: Sep. 27, 2016

(54) MEDICAL IMAGE PROCESSING APPARATUS FOR EXAMINING AN EYE TO DETERMINE THE STAGE OF GLAUCOMA

(75) Inventor: Keiko Yonezawa, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 553 days.

(21) Appl. No.: 12/854,049

(22) Filed: Aug. 10, 2010

(65) Prior Publication Data

US 2011/0046480 A1    Feb. 24, 2011

Related U.S. Application Data

(63) Continuation of application No. PCT/JP2010/000729, filed on Feb. 8, 2010.

(30) Foreign Application Priority Data

Apr. 16, 2009 (JP) ................................. 2009-100374

(51) Int. Cl.
*A61B 6/00* (2006.01)
*A61B 3/10* (2006.01)
(Continued)

(52) U.S. Cl.
CPC ............. *A61B 3/102* (2013.01); *G06T 7/0012* (2013.01); *A61B 5/4893* (2013.01); *G06T 2207/10024* (2013.01); *G06T 2207/10101* (2013.01); *G06T 2207/30041* (2013.01)

(58) Field of Classification Search
CPC .......... G06T 2207/30041; G06T 2207/10101
USPC .................. 382/117, 128; 351/205; 600/425
See application file for complete search history.

(56) References Cited

U.S. PATENT DOCUMENTS 5,868,134 A    2/1999  Sugiyama et al.
6,053,865 A *  4/2000  Sugiyama et al. ............ 600/300
(Continued)

FOREIGN PATENT DOCUMENTS

JP    H07-136122 A    5/1995
JP    2000-262472 A   9/2000
(Continued)

OTHER PUBLICATIONS

Ajtony et al, Relationship between Visual Field Sensitivity and Retinal Nerve Fiber Layer Thickness as Measured by Optical Coherence Tomography, Investigative Ophthalmology & Visual Science, Jan. 2007, vol. 48, No. 1.*
(Continued)

*Primary Examiner* — Serkan Akar
(74) *Attorney, Agent, or Firm* — Carter, DeLuca, Farrell & Schmidt, LLP

(57) ABSTRACT

This invention is directed towards a medical image processing apparatus capable of providing effective information on glaucoma by integrating the tomographic image of the retina obtained by an optical coherence tomograph (OCT: Optical Coherence Tomography) and visual function information obtained by a perimeter. The medical image processing apparatus associates visual field measurement results with a fundus camera image (S420). The medical image processing apparatus registers, on the fundus camera image associated with the visual field measurement results, a layer thickness distribution which is obtained from an OCT tomographic image and indicates the thickness of the nerve fiber layer in the retina layer of an eye to be examined (S440). After that, the medical image processing apparatus presents information indicating glaucoma of the eye to be examined, based on the layer thickness distribution registered on the fundus camera image, and the visual field measurement results (S470).

14 Claims, 13 Drawing Sheets

(51) Int. Cl.
  *G06T 7/00* (2006.01)
  *A61B 5/00* (2006.01)

(56) References Cited

U.S. PATENT DOCUMENTS

| | | | |
|---|---|---|---|
| 6,318,860 B1 | 11/2001 | Suzumura | |
| 2004/0254154 A1* | 12/2004 | Ashton | 514/179 |
| 2007/0038040 A1* | 2/2007 | Cense et al. | 600/310 |
| 2007/0243521 A1* | 10/2007 | Zuckerman | A61B 5/14546 435/4 |
| 2008/0100612 A1* | 5/2008 | Dastmalchi et al. | 345/418 |
| 2008/0266520 A1* | 10/2008 | Spaide | 351/206 |
| 2009/0033870 A1* | 2/2009 | Hangai et al. | 351/206 |
| 2009/0119021 A1* | 5/2009 | Schuett et al. | 702/19 |
| 2009/0123036 A1* | 5/2009 | Huang et al. | 382/117 |
| 2009/0123044 A1* | 5/2009 | Huang et al. | 382/128 |
| 2011/0046480 A1* | 2/2011 | Yonezawa | 600/425 |

FOREIGN PATENT DOCUMENTS

| | | |
|---|---|---|
| JP | 2001-520067 A | 10/2001 |
| JP | 2008-029731 A | 2/2008 |
| JP | 2008-518740 A | 6/2008 |
| JP | 2009-034480 A | 2/2009 |
| WO | 2006-052479 A | 5/2006 |

OTHER PUBLICATIONS

English Translation of Naohito of JP2008029731, Feb. 14, 2008.*
Office Action for Counterpart Japanese Application No. 2009-100374 dated Nov. 26, 2012.

* cited by examiner

MEDICAL IMAGE PROCESSING APPARATUS FOR EXAMINING AN EYE TO DETERMINE THE STAGE OF GLAUCOMA

CROSS REFERENCE

This application is a continuation of International Application No. PCT/JP2010/000729, filed Feb. 8, 2010, which claims the benefit of Japanese Patent Application No. 2009-100374, filed Apr. 16, 2009, both of which are hereby incorporated by reference in their entireties.

TECHNICAL FIELD

The present invention relates to a medical image processing apparatus and control method thereof.

BACKGROUND ART

These days, as the number of modalities used for diagnosis increases, a diagnosis is made by comprehensively judging pieces of information obtained by a plurality of modalities. For example, in an eye clinic, an optical coherence tomograph (OCT: Optical Coherence Tomography) is introduced into the clinical site in addition to a fundus camera and perimeter which have been used conventionally. The OCT provides a new finding, that is, the tomographic image of the retina.

An increasing number of modalities boosts the need to clarify the relationship between pieces of information provided by respective modalities. For example, in patent literature 1, visual field abnormality data obtained by a perimeter, and an abnormality around the optic disk or an optic nerve fiber layer defect that is obtained from a fundus camera image are listed and presented using fundus coordinates defined based on the direction along which the nerve fiber runs. Patent literature 2 proposes a perimeter capable of designating a visual field measurement portion on a fundus camera image. This perimeter can be used to obtain the visual field sensitivity of a portion regarded to be abnormal in a fundus camera image.

PRIOR ART DOCUMENTS

Patent Literature

PLT1: Japanese Patent Laid-Open No. 7-136122
PLT2: Japanese Patent Laid-Open No. 2000-262472

SUMMARY OF INVENTION

Technical Problem

In patent literatures 1 and 2, pieces of abnormality information obtained from a fundus camera image and perimeter are listed and presented, but association with OCT is not mentioned. For glaucoma, it is known that a structural abnormality is detected first and then a functional abnormality is detected by a perimeter. Although the structural abnormality can be detected even from findings of the fundus camera image, the OCT can more appropriately grasp an early change of the layer thickness and a change of the 3D structure. There is no diagnosis support that associates OCT findings with findings obtained from the perimeter and fundus camera image.

The present invention has been made to overcome the conventional drawbacks, and has as its object to provide effective information on glaucoma by integrating the tomographic image of the retina obtained by OCT and visual function information obtained by a perimeter.

Solution to Problem

According to an aspect of the present invention, a medical image processing apparatus includes acquiring means for acquiring an OCT tomographic image of an eye to be examined that is obtained by an optical coherence tomograph, a fundus camera image obtained by a fundus camera, and a visual field measurement result obtained by a perimeter, associating means for associating the visual field measurement result with the fundus camera image, detecting means for detecting, from the OCT tomographic image, a distribution of a layer thickness indicating a thickness of a nerve fiber layer in a retina layer of the eye to be examined, registration means for registering the distribution of the layer thickness on the fundus camera image associated with the visual field measurement result, and presenting means for presenting information indicating glaucoma of the eye to be examined, based on the distribution of the layer thickness that is registered on the fundus camera image, and the visual field measurement result.

Advantageous Effects of Invention

The present invention can provide effective information on glaucoma by integrating the tomographic image of the retina obtained by OCT and information of the visual function obtained by a perimeter.

Further features of the present invention will become apparent from the following description of exemplary embodiments with reference to the attached drawings. In the accompanying drawings, the same reference numerals denote the same or similar parts.

BRIEF DESCRIPTION OF DRAWINGS

The accompanying drawings, which are incorporated in and constitute a part of the specification, illustrate embodiments of the invention and, together with the description, serve to explain the principles of the invention.

DESCRIPTION OF EMBODIMENTS

Preferred embodiments of the present invention will be described in detail below with reference to the accompanying drawings. Note that the present invention is not limited to the following embodiments, and the embodiments are merely examples advantageous for practicing the invention. Not all combinations of features described in the following embodiments are indispensable as solutions to problems by the present invention.

First Embodiment

Figure 3:
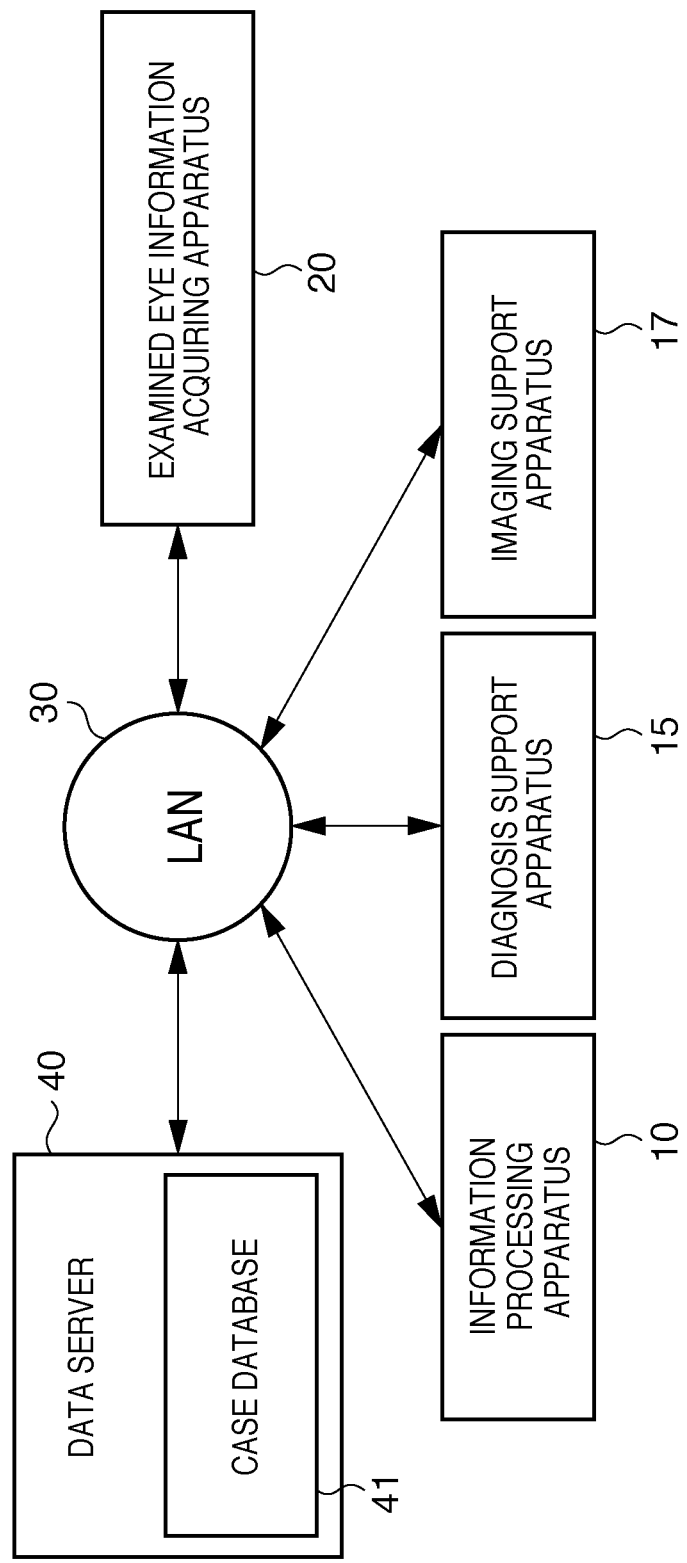
FIG. 3 is a block diagram showing the arrangement of a medical image processing apparatus according to the first embodiment.

As shown in FIG. 3, a medical image processing apparatus in the first embodiment includes, for example, an information processing apparatus 10 and diagnosis support apparatus 15. The information processing apparatus 10 and diagnosis support apparatus 15 are connected to an examined eye information acquiring apparatus 20 and data server 40 via a local area network (LAN) 30. These devices are connected via an interface such as Ethernet®, USB interface, or IEEE1394 interface. These devices may also be connected via an external network such as the Internet. The data server 40 contains a case database 41 in which glaucoma cases are accumulated. The case database 41 stores glaucoma cases at different stages from early glaucoma to late one.

The examined eye information acquiring apparatus 20 is a general term for apparatus that acquire measurement data of a fundus camera, optical coherence tomograph (OCT), and perimeter. The examined eye information acquiring apparatus 20 images an eye to be examined (not shown) and measures visual field sensitivity in response to a manipulation by an operator (not shown). The examined eye information acquiring apparatus 20 transmits the obtained image and other kinds of information to the diagnosis support apparatus 15 and data server 40.

Figure 1:
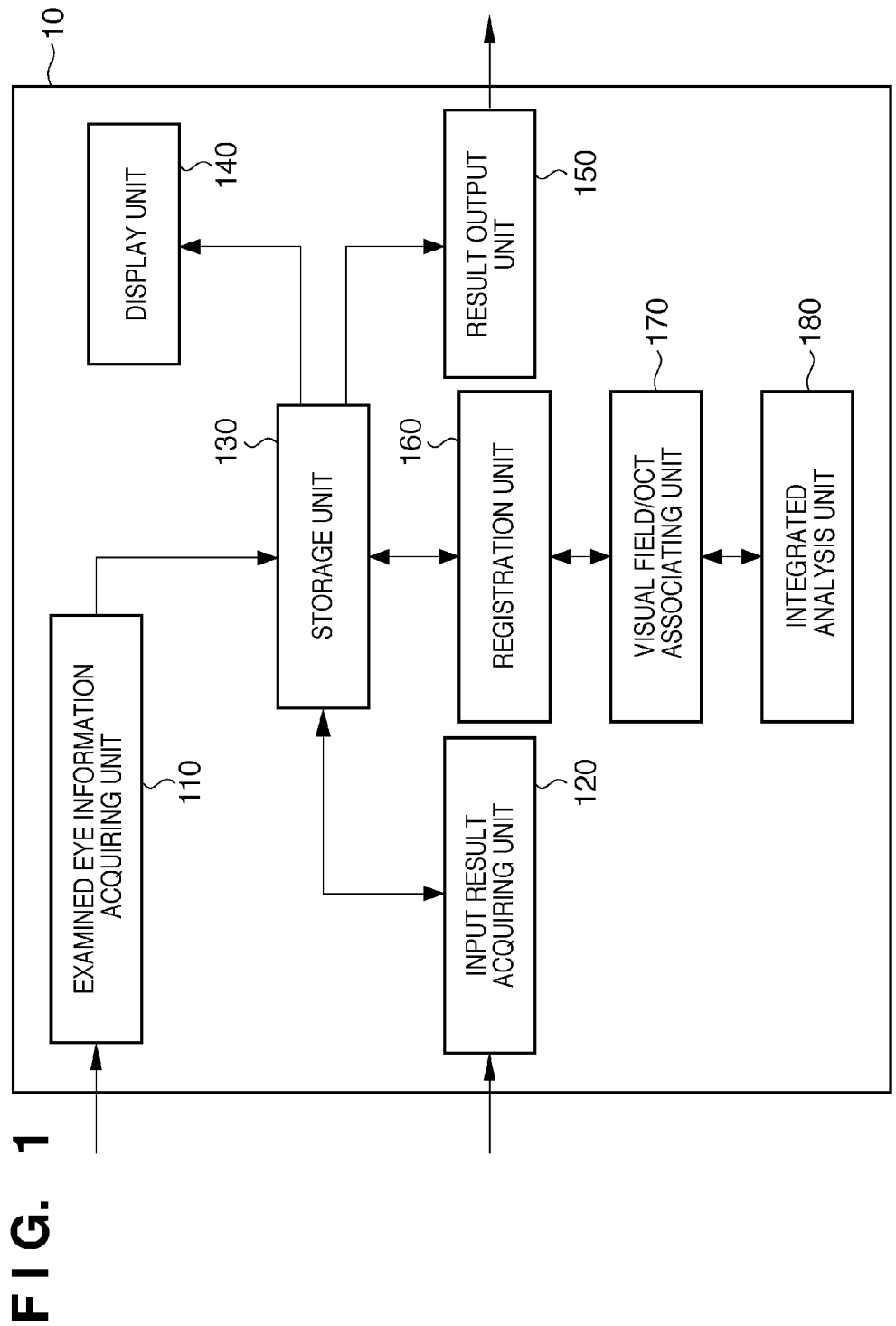
FIG. 1 is a block diagram showing the functional arrangement of an information processing apparatus according to the first embodiment.

Information processing in the embodiment is divided into pre-processing executed prior to an actual diagnosis, and diagnosis support processing using the result of the pre-processing. FIG. 1 is a block diagram showing the functional arrangement of the information processing apparatus 10 concerning pre-processing in the embodiment. An examined eye information acquiring unit 110 acquires the testing result of an examined eye. An input result acquiring unit 120 acquires an input from the operator (not shown). A registration unit 160 associates the testing results of the examined eye. A visual field/OCT associating unit 170 associates the visual field sensitivity with the layer thickness based on the result of association by the registration unit 160. Based on the result of association by the visual field/OCT associating unit 170, an integrated analysis unit 180 sets a criterion for determining whether the examined eye suffers glaucoma. A storage unit 130 saves testing results obtained from the examined eye information acquiring unit 110, inputs obtained from the input result acquiring unit 120, and analysis results obtained by the registration unit 160 and integrated analysis unit 180. A display unit 140 displays contents saved in the storage unit 130 on a monitor (not shown) or the like. A result output unit 150 transmits contents saved in the storage unit 130 to the data server 40.

Figure 2:
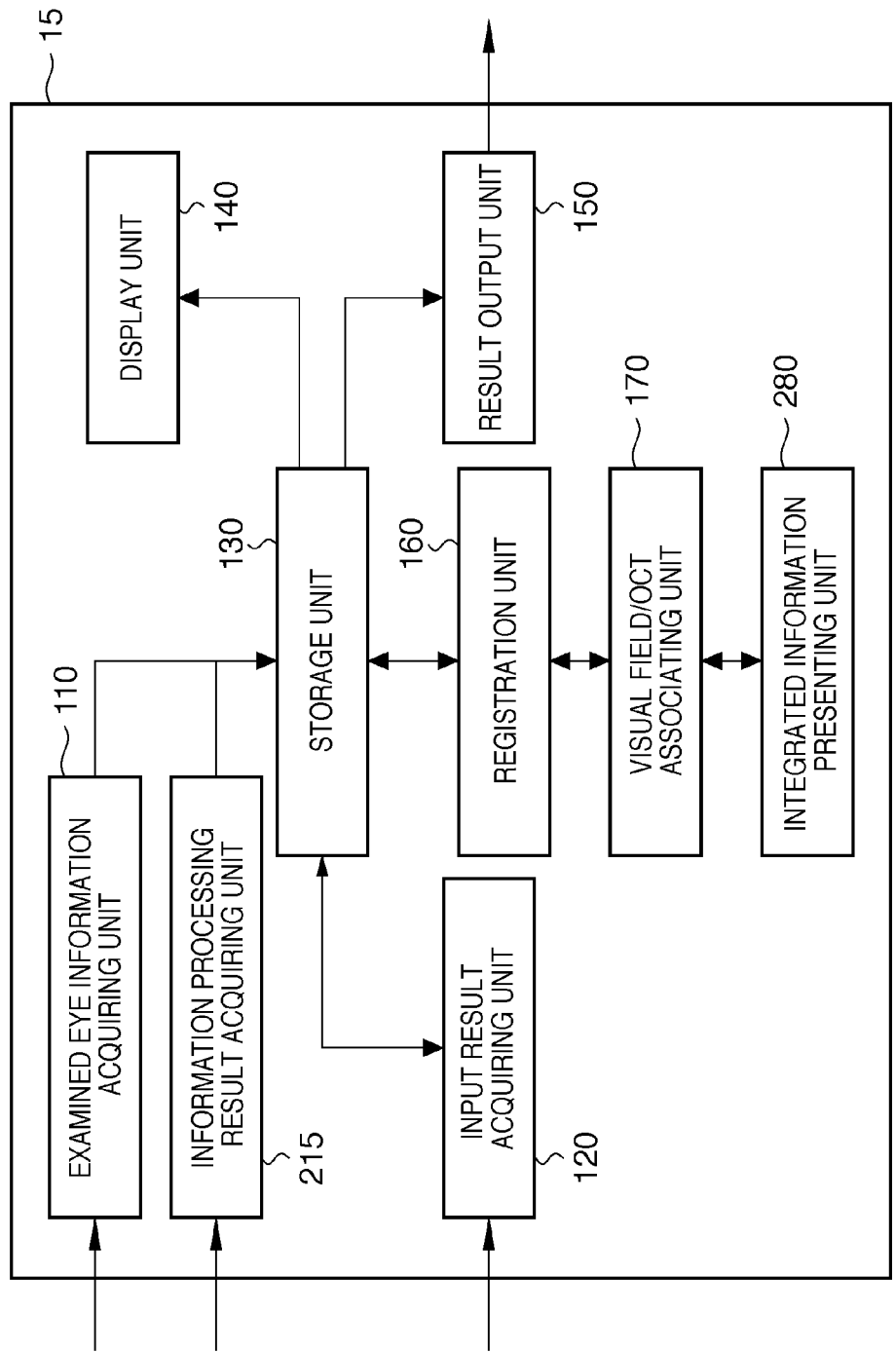
FIG. 2 is a block diagram showing the functional arrangement of a diagnosis support apparatus according to the first embodiment.

FIG. 2 is a block diagram showing the functional arrangement of the diagnosis support apparatus 15 concerning diagnosis support processing. An information processing result acquiring unit 215 is added to the functional arrangement of the information processing apparatus 10 in FIG. 1. The integrated analysis unit 180 is replaced with an integrated information presenting unit. The information processing result acquiring unit 215 acquires the result of processing in the information processing apparatus. An integrated information presenting unit 280 sets presentation information which supports diagnosis for a case input from the examined eye information acquiring unit 110.

Figure 4:
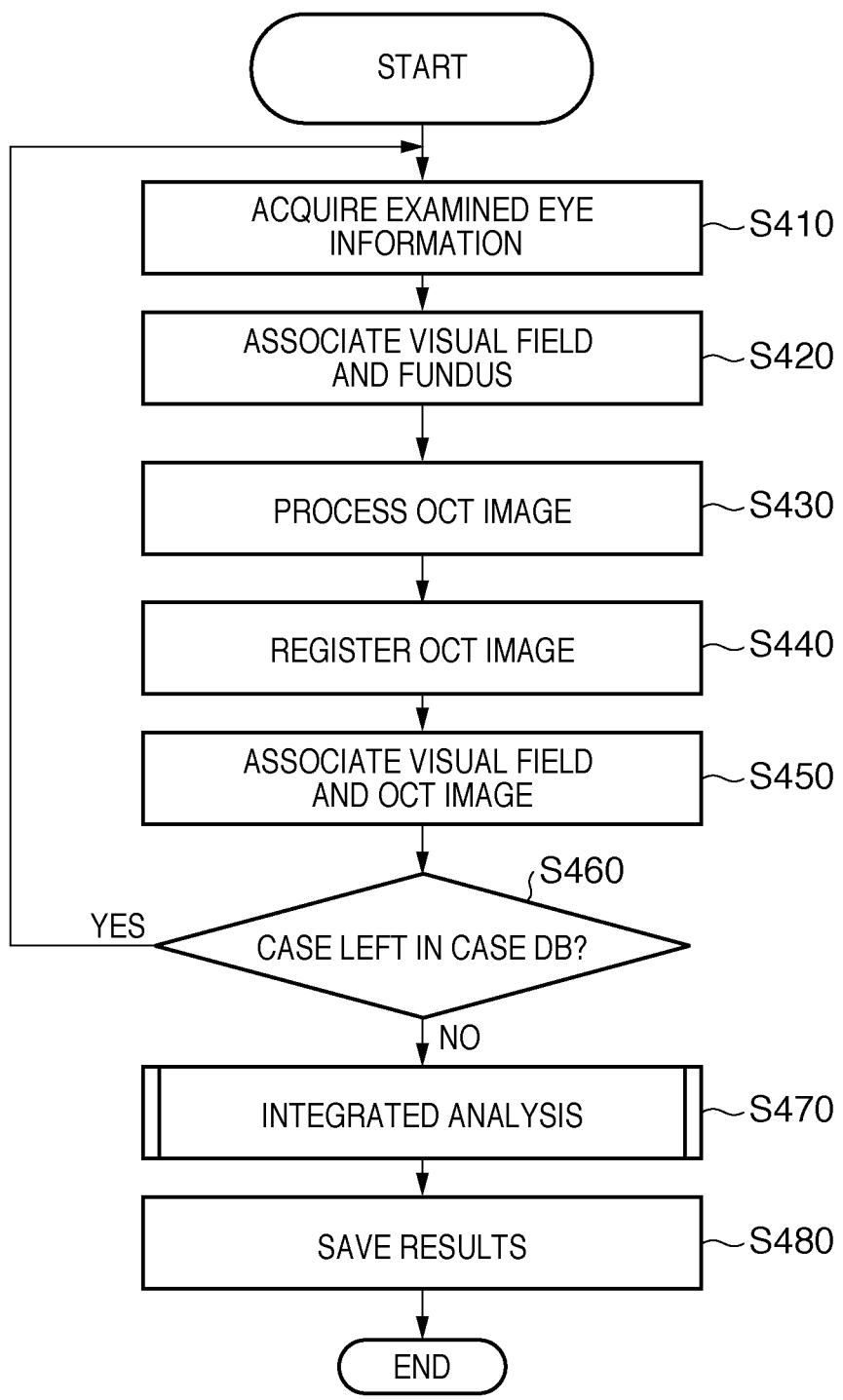
FIG. 4 is a flowchart showing a processing sequence by the information processing apparatus according to the first embodiment.

A concrete processing sequence in pre-processing executed by the information processing apparatus 10 when the information processing apparatus 10 is applied to a glaucoma diagnosis support system will be explained with reference to the flowchart of FIG. 4. The examined eye information acquiring unit 110 acquires the fundus camera image, visual field measurement results, and OCT image of the same subject from the case database 41 in the data server 40 (S410). The examined eye information acquiring unit 110 transmits the acquired information to the storage unit 130.

The registration unit 160 acquires the visual field measurement results and fundus camera image from the storage unit 130. Measurement of the visual field is to measure responses of a subject to bright points which are presented to an eye to be examined and are different in size, brightness, and position. For example, static perimeters such as the Humphrey perimeter and Octopus perimeter, and kinetic perimeters such as the Goldmann perimeter are known. To detect a visual field abnormality of early glaucoma, testing using a static perimeter is effective, and various glaucoma testing programs are prepared. The type of perimeter and the measurement program are not limited to these examples.

First, the optic disk and macula lutea are detected from the fundus camera image. The optic disk is detected from the fundus camera image using, for example, a blood vessel. The position of the optic disk is detected based on a characteristic in which vascular plexuses spreading in the retina converge at the optic disk. The macula lutea is detected based on a characteristic in which the brightness becomes minimum at the central pit than the periphery.

The measurement points of the obtained visual field measurement results are associated with positions on the fundus camera image (S420). More specifically, the center of vision fixation serving as the center of visual field measurement is made to correspond to the central pit serving as the center of the macula lutea, and the blind spot is made to correspond to the optic disk. The scale of the fundus camera image and that of the positions of the visual field measurement results are made to coincide with each other. The positions of the macula lutea and optic disk detected from the fundus camera image, and those of the center of vision fixation and the blind spot which are obtained from the visual field measurement results are made to correspond to each other. Then, the scale of the fundus camera image and that of the positions of the visual field measurement results are made to coincide with each other. Accordingly, the visual field measurement results are associated with the fundus camera image. The storage unit 130 stores the obtained results.

The registration unit 160 performs OCT image processing (S430). More specifically, the registration unit 160 acquires an OCT tomographic image from the storage unit 130 and extracts the retina layer from the tomographic image.

Figure 5:
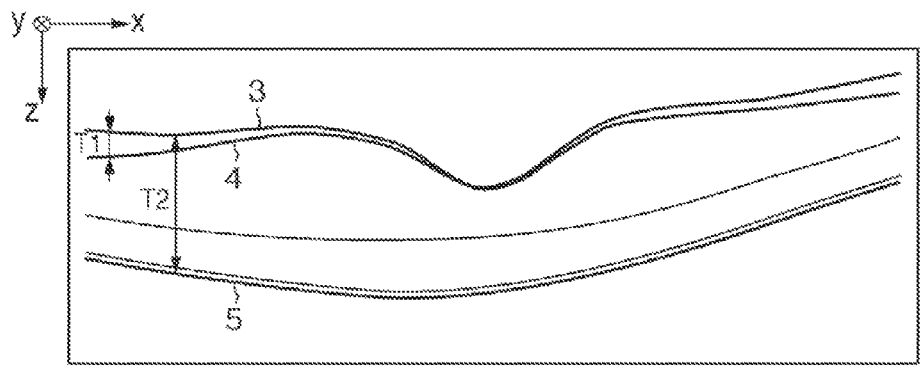
FIG. 5 is a view for explaining the layered structure of the retina.

FIG. 5 is a schematic view showing the retina layer structure around the macula lutea. An internal limiting membrane 3, nerve fiber layer boundary 4, and pigmented retina layer boundary 5 are detected from the tomographic image. A thickness T1 of the nerve fiber layer and a thickness T2 of the entire retina layer are obtained. However, layers of interest are not limited to these two layers.

A concrete processing method of detecting the boundary between layers will be explained. A 3D tomographic image to be processed is regarded as a set of 2D tomographic images (B-scan images). Each 2D tomographic image undergoes the following 2D image processing. First, a 2D tomographic image of interest undergoes smoothing filtering processing to remove a noise component. Then, edge components are detected from the tomographic image, and several segments are extracted as layer boundary candidates based on the connectivity of the edge components. The top segment is selected as the internal limiting membrane 3 from the candidates. A segment immediately below the internal limiting membrane 3 is selected as the nerve fiber layer boundary 4. The bottom segment is selected as the pigmented retina layer boundary 5.

The detection precision may be increased by applying a dynamic contour method such as the Snake method or level set method, using these segments as initial values. The boundary between layers may be detected using the graph cut method or the like. Note that boundary detection using the dynamic contour method or graph cut method may be executed three-dimensionally for a 3D tomographic image, or applied two-dimensionally to each 2D tomographic image on the premise that the 3D tomographic image to be processed is a set of 2D tomographic images. The method of detecting the boundary between layers is not limited to them, and any method is available as long as the boundary between layers can be detected from the tomographic image of an eye.

Based on the detected boundaries between layers, the registration unit 160 quantifies the thicknesses of the nerve fiber layer and entire retina layer. First, the registration unit 160 calculates the thickness T1 of the nerve fiber layer by obtaining the difference in z-coordinate between the nerve fiber layer boundary 4 and the internal limiting membrane 3 at each coordinate point on the x-y plane. Similarly, the registration unit 160 calculates the thickness T2 of the entire retina layer by obtaining the difference in z-coordinate between the pigmented retina layer boundary 5 and the internal limiting membrane 3.

Processing proceeds using the nerve fiber layer thickness more directly indicating a change of glaucoma. Thus, the layer thickness means the thickness of the nerve fiber layer. However, it is known that the retina is made up of a plurality of layers, and the display of the layer thickness in this proposal is not limited to the nerve fiber layer.

The registration unit 160 further detects the coordinates of the central pit using the internal limiting membrane 3. More specifically, the registration unit 160 detects, as the central pit, a point where the z-coordinate of the detected internal limiting membrane 3 becomes maximum near the center of the tomographic image. The registration unit 160 outputs these results obtained in S430 to the storage unit 130.

The registration unit 160 registers, on the visual field measurement results and fundus camera image which have been associated with each other in S420, the layer thickness distribution of the nerve fiber layer that has been obtained from the OCT tomographic image in S430 (S440).

An image is created by integrating the pixel values of corresponding z-coordinates on the x-y plane of the OCT 3D tomographic image. The created 2D image will be called an OCT projection image, and the OCT projection image is registered on the fundus camera image.

As a known method of registering an OCT projection image on a fundus camera image, blood vessels are extracted from the two images and aligned with each other, thereby registering the two types of images. Registration is further done to align the macula lutea of the fundus camera image detected in S420 with that of the OCT detected in S430. The registration unit 160 outputs these results obtained in S440 to the storage unit 130.

By registering the OCT projection image on the fundus camera image, visual field sensitivity information associated with the fundus camera image can be associated with layer thickness information of the nerve fiber layer associated with the OCT projection image.

The visual field/OCT associating unit 170 normalizes the layer thickness of the OCT image registered in S440 by using the mean distribution value of the OCT layer thickness in a normal case (S450).

The mean distribution value in a normal case is a layer thickness distribution attained by superposing the OCT tomographic images of a plurality of normal cases and averaging layer thicknesses at respective positions. In this case, layer thicknesses at respective positions in the OCT image registered in S440 are normalized by setting the mean value of a normal case to "1". However, the layer thickness at the central pit is excluded in normalization because the thickness of the nerve fiber layer is almost 0 at the central pit at the center of the macula lutea.

The OCT/visual field associating unit 170 associates the normalized layer thicknesses with the visual field measurement results which have been associated with corresponding regions in S440. The region is attained by segmenting a range where visual field measurement is done within the OCT imaging range. The minimum region is a pixel.

Figure 6:
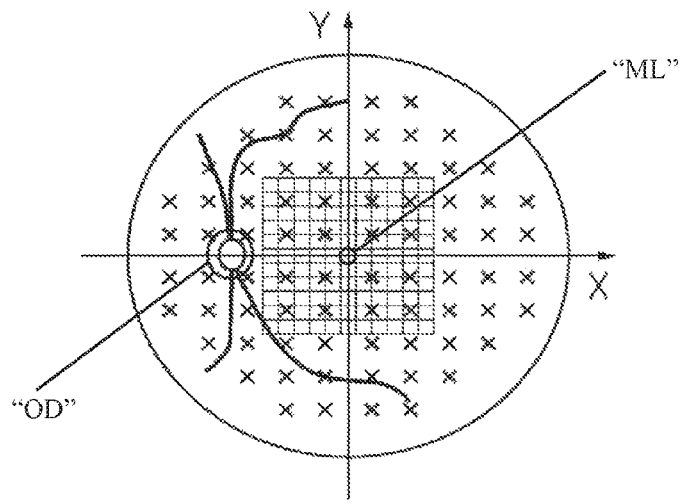
FIG. 6 is a view for explaining a state in which a fundus camera image, visual field measurement results, and an OCT projected image are registered according to the first embodiment.

FIG. 6 exemplifies the result of registering an imaging region, fundus camera image, and visual field measurement results when the macula lutea and its periphery are imaged in OCT. FIG. 6 also shows an example of segmenting the OCT imaging region. FIG. 6 shows an example of segmenting the OCT imaging region of the macula lutea into 11×11. The average layer thickness and visual field sensitivity in each region are calculated to create a graph.

The region segmentation utilizes a characteristic in which nerve fibers run without crossing above and under a line connecting the macula lutea "ML" and optic disk "OD." More specifically, a straight line which connects the center of the macula lutea "ML" and the optic disk "OD" is defined. A coordinate system in which the X-axis is parallel to the straight line, the Y-axis is perpendicular to it, and the center matches the central pit at the center of the macula lutea "ML" is defined. The region segmentation is executed along the X- and Y-axes.

The mean of the layer thickness is a mean value in each region in the layer thickness distribution obtained by OCT in S430. The mean value of the visual field sensitivity is calculated as follows based on visual field sensitivity values at measurement points.

Figure 7:
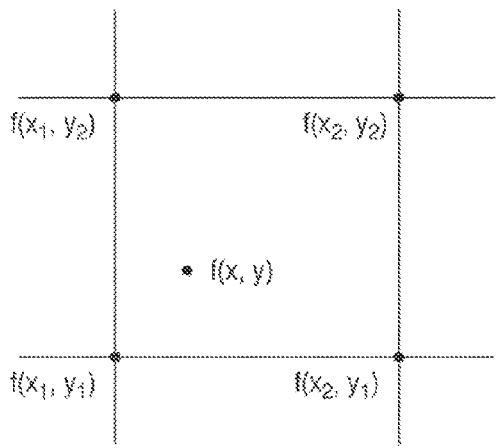
FIG. 7 is a view showing the positional relationship when calculating values at points other than visual field sensitivity measurement points according to the first embodiment.

The value of a visual field sensitivity f(x,y) at a given point (x,y) is calculated in accordance with equation (1) using values at points (x1,y1), (x1,y2), (x2,y1), and (x2,y2) around the point having undergone visual field measurement. FIG. 7 shows the positional relationship between points.

$$f(x, y) = \frac{1}{(x_2 - x_1)(y_2 - y_1)}$$
$$[(x_2 - x)(y_2 - y)f(x_2, y_2) + (x - x_1)(y_2 - y)f(x_1, y_2) +$$
$$(x_2 - x)(y - y_1)f(x_2, y_1) + (x - x_1)(y - y_1)f(x_1, y_1)] \quad (1)$$

The measurement point of visual field sensitivity does not match the lattice point of region segmentation in FIG. 7. Visual field sensitivity values obtained at respective points in this way are averaged in each region, attaining the visual field sensitivity in the region. The thickness of the nerve fiber layer and the visual field sensitivity are associated with each other for each region, and saved in the storage unit 130.

The OCT/visual field associating unit 170 determines whether there is a case left in the case database 41 (S460). If a case is left, the process returns to S410 to repeat the foregoing processing. If all cases in the case database 41 have undergone the processing, the process advances to processing in S470.

In S470, based on a change of the layer thickness and a change of the visual field sensitivity that have been associated with each other in S450, the integrated analysis unit 180 generates a criterion for determining whether the eye suffers glaucoma.

Figure 8:
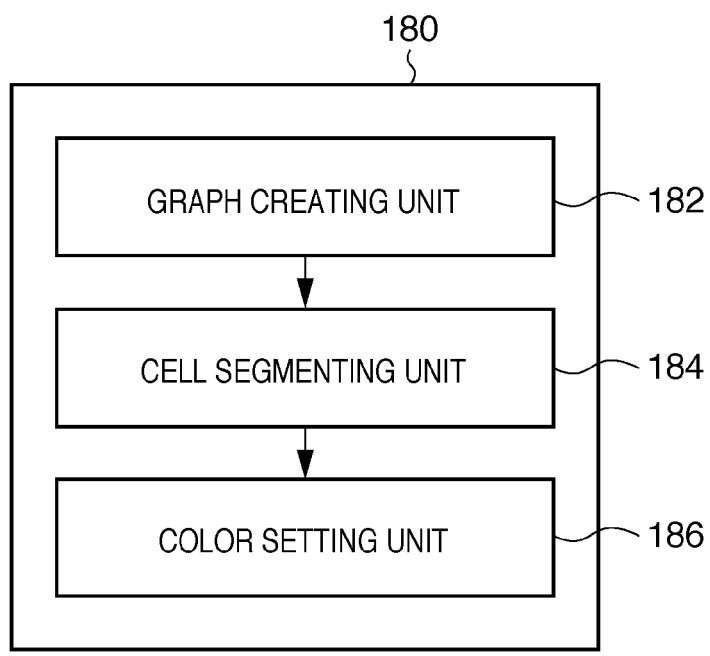
FIG. 8 is a block diagram showing details of the functional arrangement of an integrated analysis unit according to the first embodiment.

As shown in FIG. 8, the integrated analysis unit 180 includes a graph creating unit 182, cell segmenting unit 184, and color setting unit 186. In this arrangement, the graph creating unit 182 creates a graph indicating the relationship between the layer thickness of a segmented region and the visual field sensitivity value that is set by the visual field/OCT associating unit 170. The graph creating unit 182 outputs the graph to the cell segmenting unit 184. The cell segmenting unit 184 segments the graph region created by the graph creating unit 182 into a plurality of cells in accordance with the layer thickness value and visual field sensitivity value, and outputs the cells to the color setting unit 186. The color setting unit 186 sets a color used in display for each cell segmented by the cell segmenting unit 184.

Figure 9:
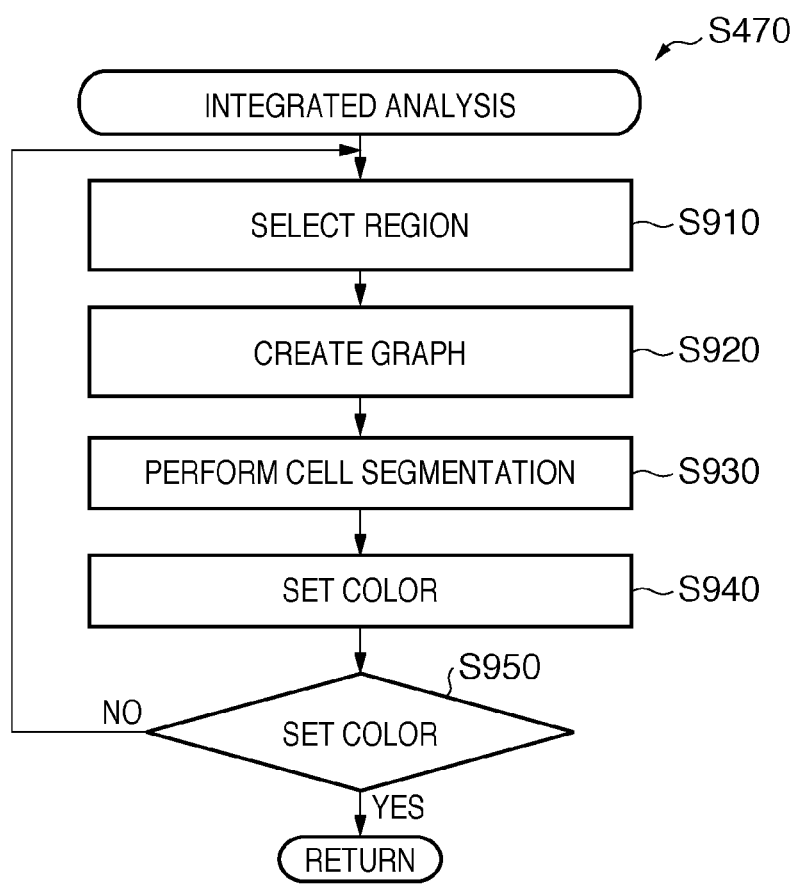
FIG. 9 is a flowchart showing an integrated analysis processing sequence according to the first embodiment.

Details of the processing in S470 will be explained with reference to the flowchart of FIG. 9. The integrated analysis unit 180 selects one of segmented regions set in S450 (S910). For all cases in the case database 41, the integrated analysis unit 180 acquires, from the storage unit 130, layer thickness values and visual field sensitivity values in the region that have been associated in S450.

Figure 10:
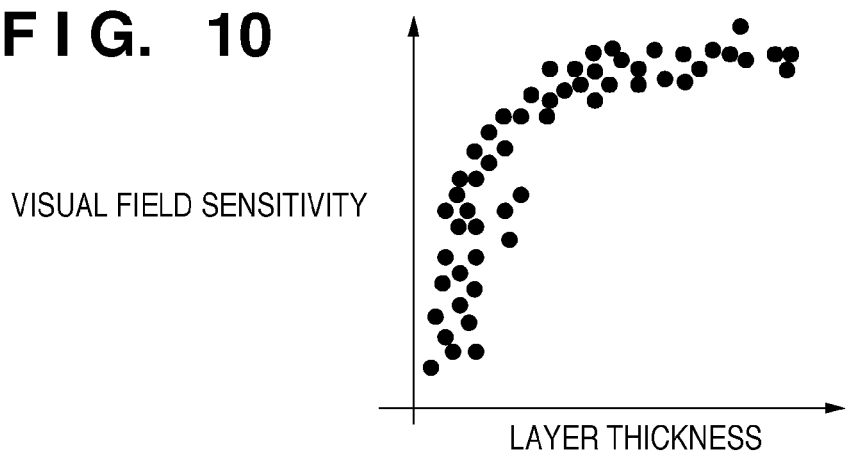
FIG. 10 is a graph showing the relationship between the layer thickness and visual field sensitivity of glaucoma according to the first embodiment.

The graph creating unit 182 creates a graph of the layer thickness values and visual field sensitivity values acquired in S910 by plotting the layer thickness along the abscissa axis and the visual field sensitivity along the ordinate axis (S920). FIG. 10 exemplifies the created graph.

The cell segmenting unit 184 segments the graph region created in S920 in accordance with the layer thickness value and visual field sensitivity value (S930). A purpose of this is to divide the selected region into cases in which the visual field sensitivity changes slightly and a change should be grasped based on the layer thickness, and those in which the visual field changes remarkably and a change should be grasped based on the visual field sensitivity. As for the visual field sensitivity, the region is segmented by every 5-db decrement. As for the layer thickness, the region is segmented by every 10% decrement. However, the segmentation method is not limited to this.

The value and range of segmentation depend on a perimeter used, presentation information, segmentation range in OCT image processing, and the like, and need to be determined in accordance with them. The relationship between a change of the layer thickness and a decrease in visual field sensitivity changes depending on the region. It is known that the decrement of the layer thickness necessary for an equivalent decrease in visual field sensitivity becomes large especially at a portion near the macula lutea. Hence, the cell segmentation method changes depending on a selected region.

The color setting unit 186 sets a color used in display for each cell segmented in S930 (S940). The color may be set to be darker for a more advanced stage.

Figure 11:
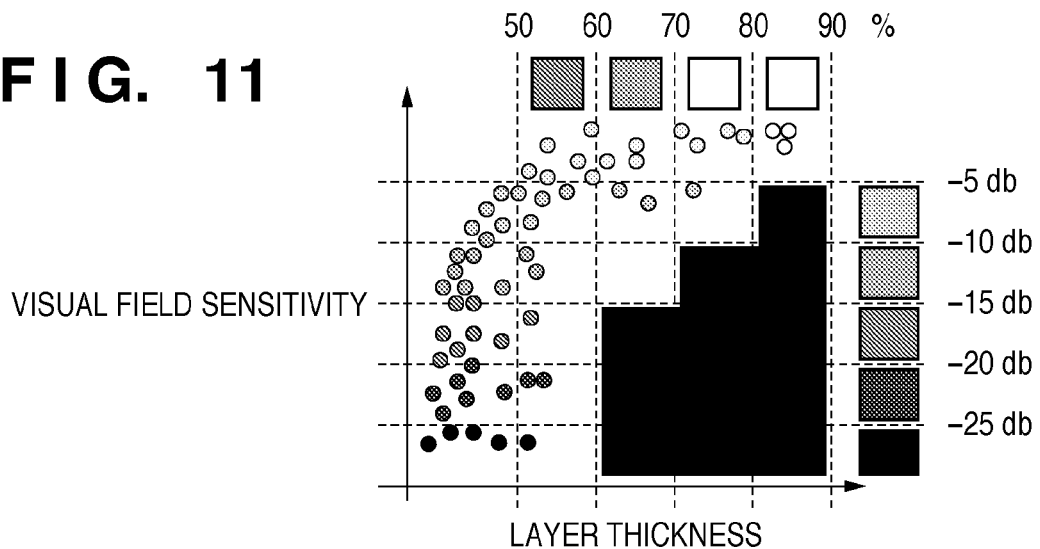
FIG. 11 is a diagram for explaining a state in which, when a graph showing the relationship between the layer thickness and the visual field sensitivity is created, the color of the graph is determined based on region segmentation according to the first embodiment.

FIG. 11 is a diagram upon the cell segmentation in S930 and the color setting in S940. In this example, both the layer thickness and visual field sensitivity are expressed by the grayscale. It is also possible to use the grayscale for the layer thickness and the color gradation for the visual field sensitivity. In this case, a region suffering a decrease in visual field sensitivity can be explicitly indicated.

In accordance with the cell segmentation executed in S930, the color setting unit 186 sets a region exhibiting a layer thickness and visual field sensitivity that deviate from those of glaucoma. More specifically, the layer thickness is sufficient, but the visual field sensitivity decreases, as indicated by regions filled in black in FIG. 11. This may simply be measurement variations, but may indicate a sign of a disease different from glaucoma. In this fashion, a cell determined to deviate from glaucoma is set, and its color is set to definitely discriminate it from other cells.

Figure 12:
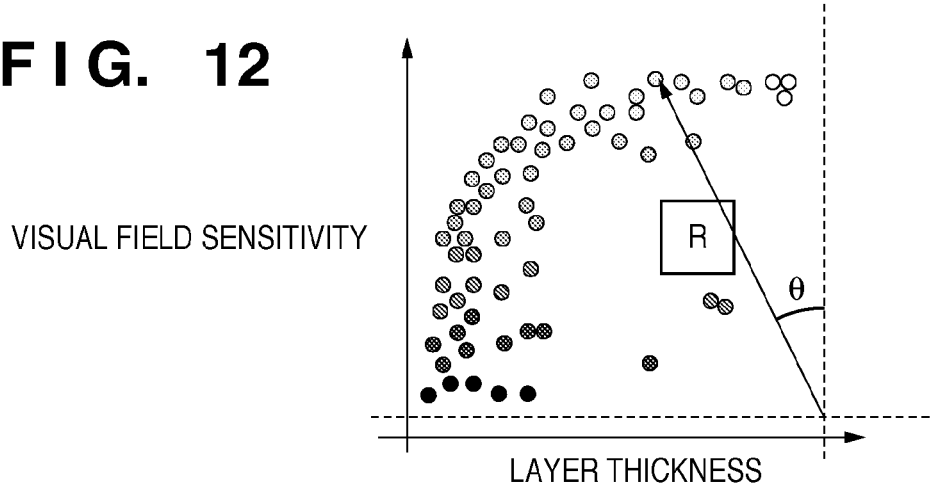
FIG. 12 is a diagram for explaining a state in which, when a graph showing the relationship between the layer thickness and the visual field sensitivity is created, the color of the graph is determined based on the polar coordinate display according to the first embodiment.

In addition, there are various color setting methods capable of representing the stage of glaucoma and explicitly indicating whether the layer thickness and visual field sensitivity deviate from those of glaucoma. For example, FIG. 12 shows a polar coordinate display whose origin is defined by a point of a 90% layer thickness and a point of a −30 db visual field sensitivity. The angle θ is an angle with respect to the ordinate axis indicating the point of the 90% layer thickness. The radius R is a distance from the origin. The scales of the layer thickness and visual field sensitivity are adjusted so that measurement points are distributed using R=1 as a center. Therefore, the angle θ can express the stage of glaucoma, and the degree of deviation from the radius R=1 can indicate the degree of deviation from glaucoma.

Consider a case in which the hue changes depending on θ and the lightness changes depending on R. The display changes from blue to red as glaucoma progresses, and changes from a bright color to black as the layer thickness and visual field sensitivity deviate from those of glaucoma. From this, the color is set using the HSV color system:

$$\text{hue} = 240 + 240\theta/\pi \quad (2)$$

$$\text{lightness} = 256 - 256|R-1| \quad (3)$$

By setting the color in this way, both the stage of glaucoma and the degree of deviation can be explicitly indicated continuously.

The integrated analysis unit 180 determines whether all segmented regions set in S450 have been selected in S910 (S950). If there is an unselected region, the process returns to S910; if all regions have been selected, the integrated analysis processing in S470 ends.

The integrated analysis unit 180 saves the analysis results in the storage unit 130, and saves them in the data server 40 via the result output unit 150 (S480).

Figure 13:
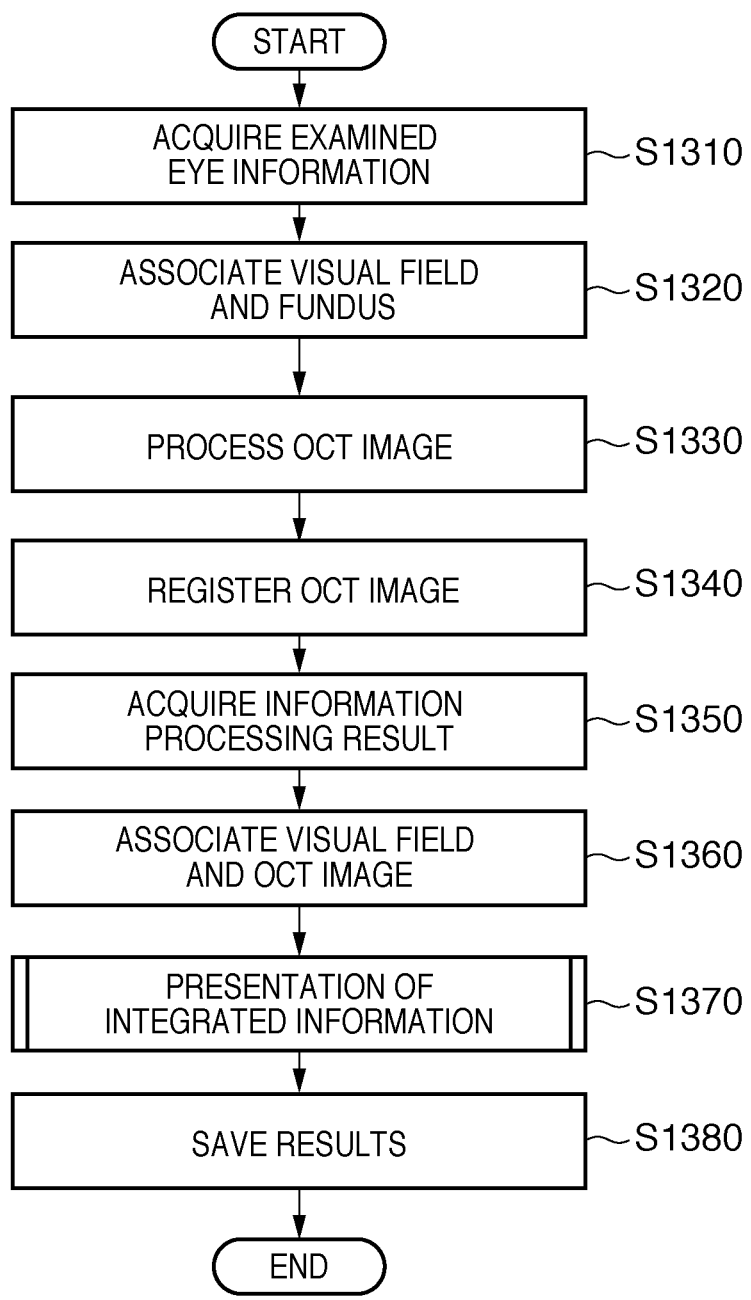
FIG. 13 is a flowchart showing a processing sequence by the diagnosis support apparatus according to the first embodiment.

A concrete processing sequence of diagnosis support processing when the diagnosis support apparatus 15 is applied to a glaucoma diagnosis support system will be explained with reference to the flowchart of FIG. 13.

The input result acquiring unit 120 externally acquires information such as the patient ID for identifying an eye to be examined (S1310). Based on the information for identifying an eye to be examined, the examined eye information acquiring unit 110 acquires, from the examined eye information acquiring apparatus 20, a fundus camera image, visual field measurement results, and an OCT image that correspond to the patient ID. The examined eye information acquiring unit 110 transmits the acquired information to the storage unit 130.

By using the same method as that in S410 and S440, the registration unit 160 registers the fundus camera image, visual field measurement results, and OCT image which have been acquired in S1310 (S1320 and S1340). The registration unit 160 transmits these results obtained in S440 to the storage unit 130.

The information processing result acquiring unit 215 acquires associated information of a visual field sensitivity and layer thickness for each region that have been saved in the data server 40 in S480 and comprehensively analyzed for a case in the case database (S1350). The information processing result acquiring unit 215 transmits the acquired information to the storage unit 130.

The visual field/OCT associating unit 170 associates the visual field sensitivity with the layer thickness of the nerve fiber layer using the fundus camera image, visual field measurement results, and OCT image which have been registered in S1340 (S1360). In this case, the same method as that in S450 is employed.

The integrated information presenting unit 280 performs integrated information presentation processing (S1370). At this time, the integrated information presenting unit 280 compares the visual field-layer thickness association result which has been obtained in S1350 for the eye to be examined, with the integrated analysis result acquired in S1360.

Figure 14:
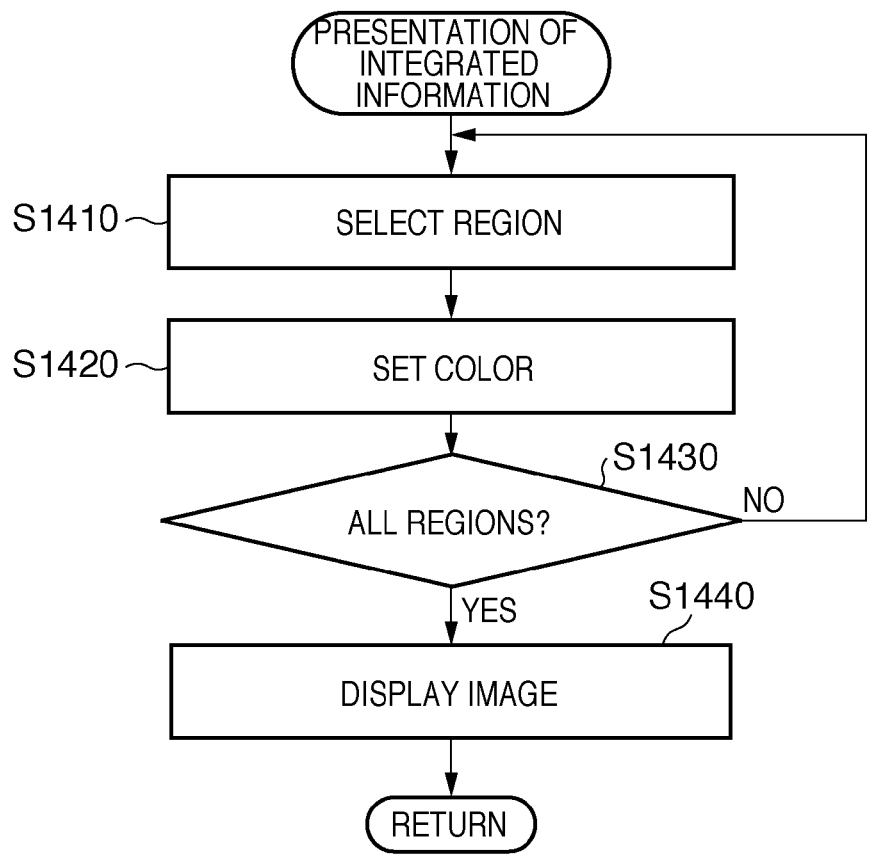
FIG. 14 is a flowchart showing integrated information presentation processing according to the first embodiment.

Details of the integrated information processing in S1370 will be described with reference to the flowchart of FIG. 14. The integrated information presenting unit 280 selects one of segmented regions set in S1350 (S1410). The integrated information presenting unit 280 acquires, from the storage unit 130, a graph and color setting created for a layer thickness value and visual field sensitivity value in the region that have been comprehensively analyzed in S480.

The integrated information presenting unit 280 acquires, from the storage unit 130, the relationship between the layer thickness and the visual field of the eye to be examined in the region that has been obtained in S1360. The integrated information presenting unit 280 compares the relationship with the graph and color setting of the region that have been acquired in S1410, thereby acquiring a color set for the relationship between the layer thickness and the visual field (S1420). The integrated information presenting unit 280 transmits these results acquired in S1420 to the storage unit 130.

The integrated information presenting unit 280 determines whether all segmented regions set in S450 have been selected in S1410 (S1430). If there is an unselected region, the process returns to S1410; if all regions have been selected, advances to S1440.

Figure 15:
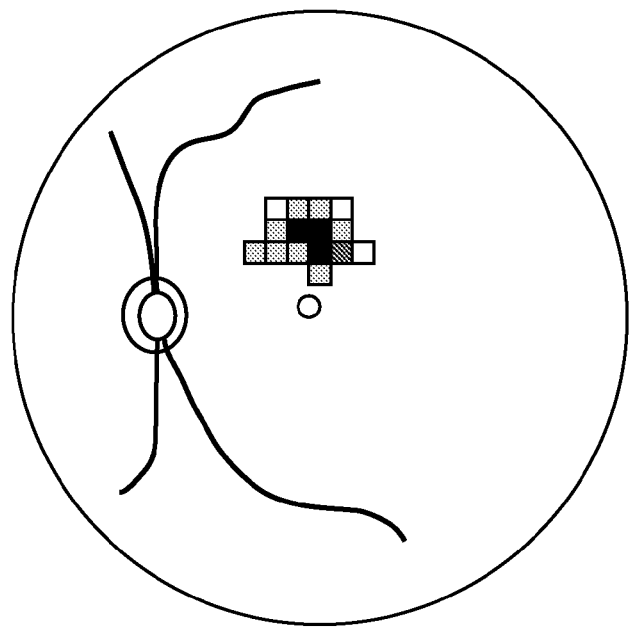
FIG. 15 is a view showing the result of setting the color on a fundus camera in consideration of the glaucoma pattern according to the first embodiment.

In S1440, the integrated information presenting unit 280 outputs, to the display unit 140, an image in which regions are filled in colors determined in S1420 for the respective regions. If no color has been set in S1420 (for example, when the visual field sensitivity decreases by smaller than 5 db or the decrement of the layer thickness is smaller than 80%), the fundus camera image is presented in this region. FIG. 15 exemplifies the image displayed at this time.

When the color of each region corresponds to a region determined in S940 not to suffer glaucoma, the integrated information presenting unit 280 outputs an alert to the display unit 140 to represent that there is a region not suffering glaucoma.

In S1380, the integrated information presenting unit 280 saves the results obtained in S1370 in the storage unit 130.

According to the first embodiment, the layer thickness of the nerve fiber layer that is attained from an OCT image, and a visual field sensitivity value obtained by a perimeter can be associated with each other together with a fundus camera image. When a change of the layer thickness and a change of the visual field sensitivity match the glaucoma pattern, the stage is given by a change of the color. When these changes deviate from the glaucoma pattern, an alert is presented. When a doctor who is a user makes a diagnosis, the relationship between pieces of information obtained by different modalities can be clarified. At the same time, the relevance with the glaucoma pattern can be explicitly indicated.

Second Embodiment

In the second embodiment, the contents of the first embodiment are applied to an OCT imaging apparatus. When an eye to be examined during ophthalmography and visual field measurement undergoes OCT imaging, the relationship between the layer thickness of the nerve fiber layer and the visual field sensitivity is explicitly indicated after OCT imaging. From this, the operator can determine whether there is a region which needs to be imaged again.

Figure 16:
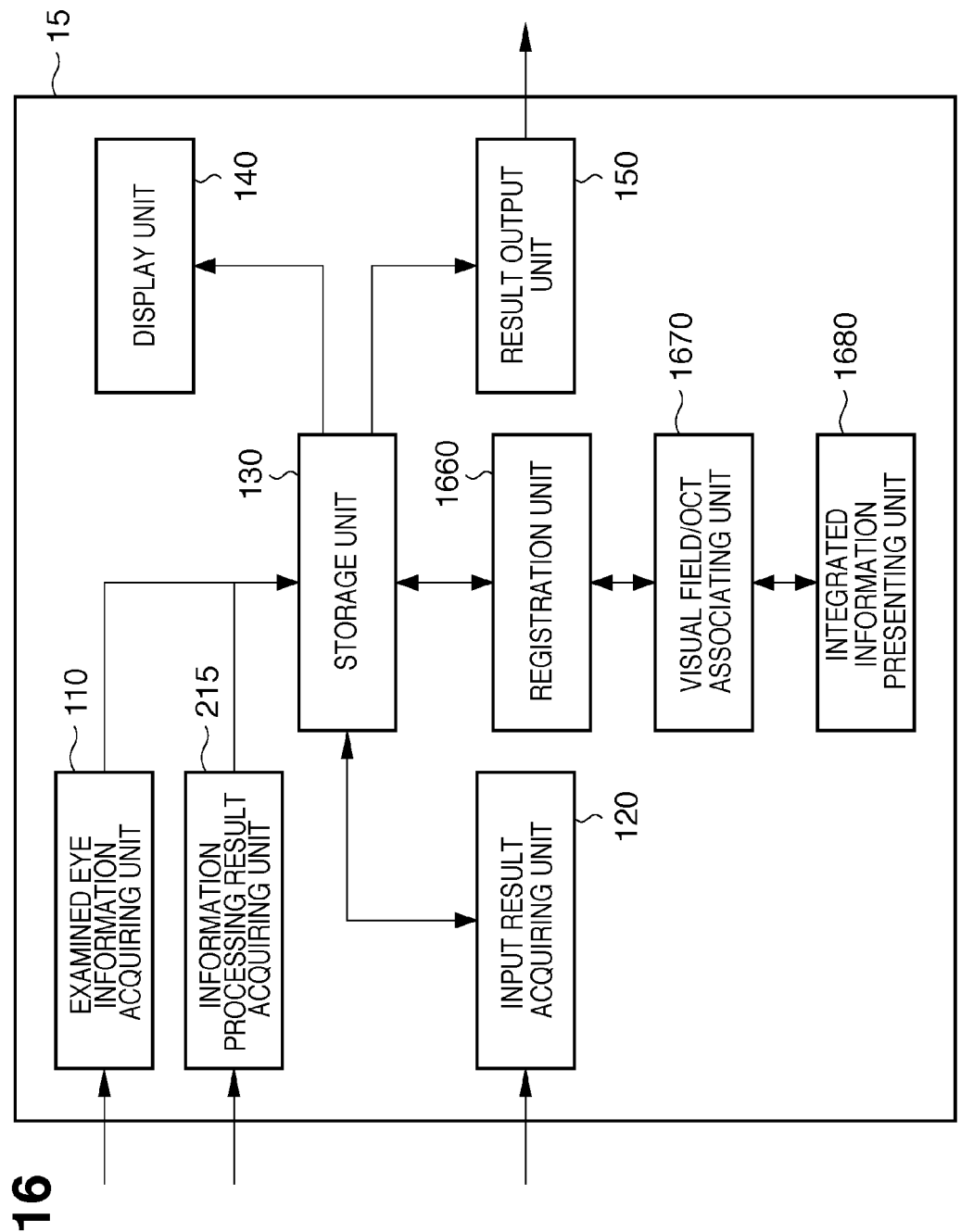
FIG. 16 is a block diagram showing the functional arrangement of a diagnosis support apparatus according to the second embodiment.

FIG. 16 is a block diagram showing the functional arrangement of a diagnosis support apparatus 15 according to the second embodiment. The contents of a registration unit 1660, visual field/OCT associating unit 1670, and integrated information presenting unit 1680 are changed from those in the diagnosis support apparatus shown in FIG. 2 in the first embodiment. In the second embodiment, as measurement results acquired by an examined eye information acquiring unit 110, a fundus camera image and visual field measurement results have already been attained by imaging, and the examined eye information acquiring unit 110 acquires the saved results. However, the examined eye information acquiring unit 110 acquires an OCT tomographic image from an examined eye information acquiring apparatus 20 in response to a request from the operator.

Figure 17:
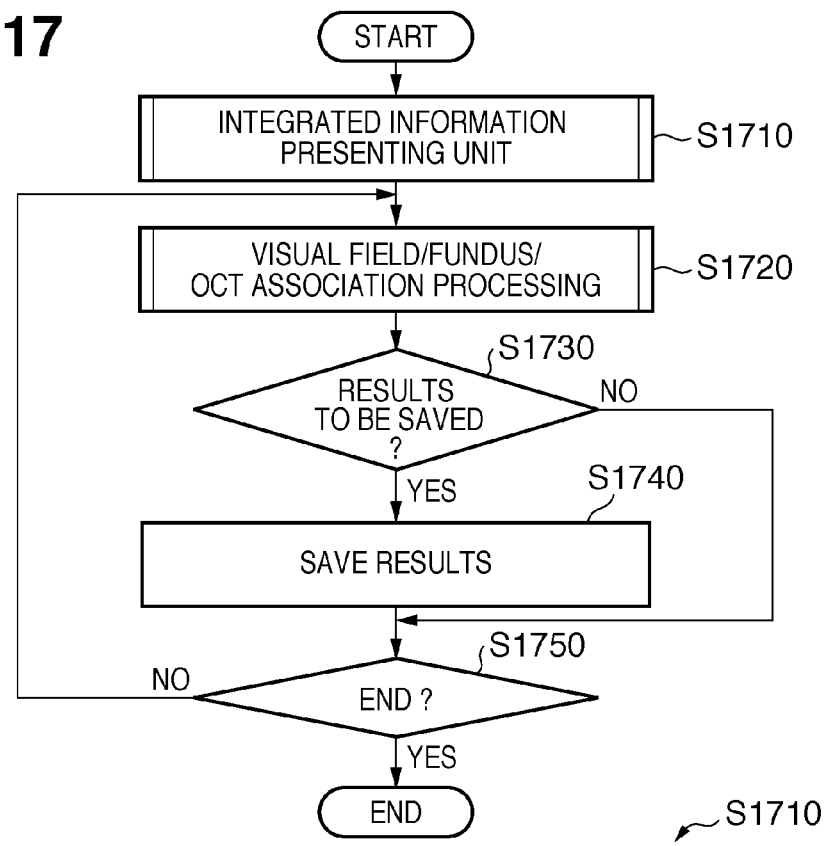
FIG. 17 is a flowchart showing a processing sequence by the diagnosis support apparatus according to the second embodiment.

A concrete processing sequence when supporting a diagnosis of glaucoma in OCT imaging by the diagnosis support apparatus in the second embodiment will be explained with reference to the flowchart of FIG. 17.

The registration unit 1660 acquires a fundus camera image already obtained by imaging, and visual field measurement results already attained by measurement, and associates the visual field measurement results with the fundus camera image (S1710). The registration unit 1660 also associates the visual field measurement results and fundus camera image with SLO (Scanning Laser Ophthalmoscope) images successively captured by the OCT imaging apparatus, thereby presenting visual field sensitivity data on the SLO.

The registration unit 1660 acquires an OCT image captured by the examined eye information acquiring apparatus 20, and executes image processing for it, acquiring the thickness of the nerve fiber layer. The visual field/OCT associating unit 1670 associates the acquired layer thickness with the visual field sensitivity acquired in S1710 (S1720).

The integrated information presenting unit 1680 compares the relationship between the associated layer thickness and visual field sensitivity with an analysis result based on a case database acquired by an information processing result acquiring unit 215, and presents the comparison result on a display unit 140 in a color explicitly indicating glaucoma. This presentation is also associated with SLO images successively captured by the examined eye information acquiring unit 110. The result is presented on the SLO.

An input result acquiring unit 120 acquires a result input by the operator, and determines whether to save the results of the processing performed in S1720 (S1730). If the processing results are to be saved, they are saved in a storage unit 130 in S1740. If the processing results are not to be saved, the process advances to S1750.

In S1750, the input result acquiring unit 120 acquires a result input by the operator, and determines whether to end the process. If the process is to end, the results saved in the storage unit 130 are saved in a data server 40 via a result output unit 150, and all processes end. If the process is not to end, it returns to S1720.

Figure 18:
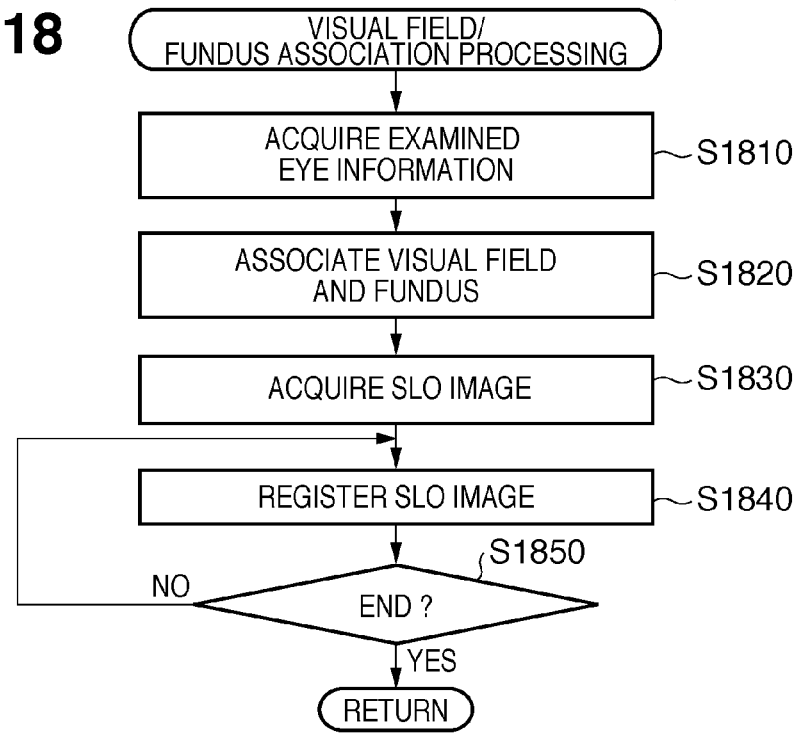
FIG. 18 is a flowchart showing visual field/fundus association processing according to the second embodiment.

The concrete contents of S1710 will be described in detail with reference to the flowchart of FIG. 18. The input result acquiring unit 120 externally acquires information such as the patient ID for identifying an eye to be examined (S1810). Based on the information for identifying an eye to be examined, the examined eye information acquiring unit 110 acquires, from the data server 40, a fundus camera image and visual field measurement results corresponding to the patient ID. The examined eye information acquiring unit 110 transmits the acquired information to the storage unit 130.

The registration unit 1660 acquires the visual field measurement results and fundus camera image from the storage unit 130. By using the same method as that in S1320, the registration unit 1660 associates the visual field measurement results with the fundus camera image (S1820). The obtained results are stored in the storage unit 130.

The examined eye information acquiring unit 110 requests the tomographic imaging device of the examined eye information acquiring apparatus 20 to transmit an SLO (Scanning Laser Ophthalmoscope) image, and acquires the transmitted SLO image (S1830). The examined eye information acquiring unit 110 transmits the acquired information to the storage unit 130.

The registration unit 1660 registers, on the SLO image saved in the storage unit 130, the fundus camera image associated with the visual field measurement results in S1820 (S1840). The display unit 140 displays an image presenting the visual field measurement results on the SLO image.

The input result acquiring unit 120 acquires a result input by the operator, and determines whether to end the process (S1850). If there is no input to end the process, the input result acquiring unit 120 determines not to end the process, and the process returns to S1830. Until the input result acquiring unit 120 receives an input to end the process or receives an OCT imaging instruction, the processing in S1710 continues to present visual field measurement results on SLO images successively transmitted from the examined eye information acquiring apparatus 20.

Figure 19:
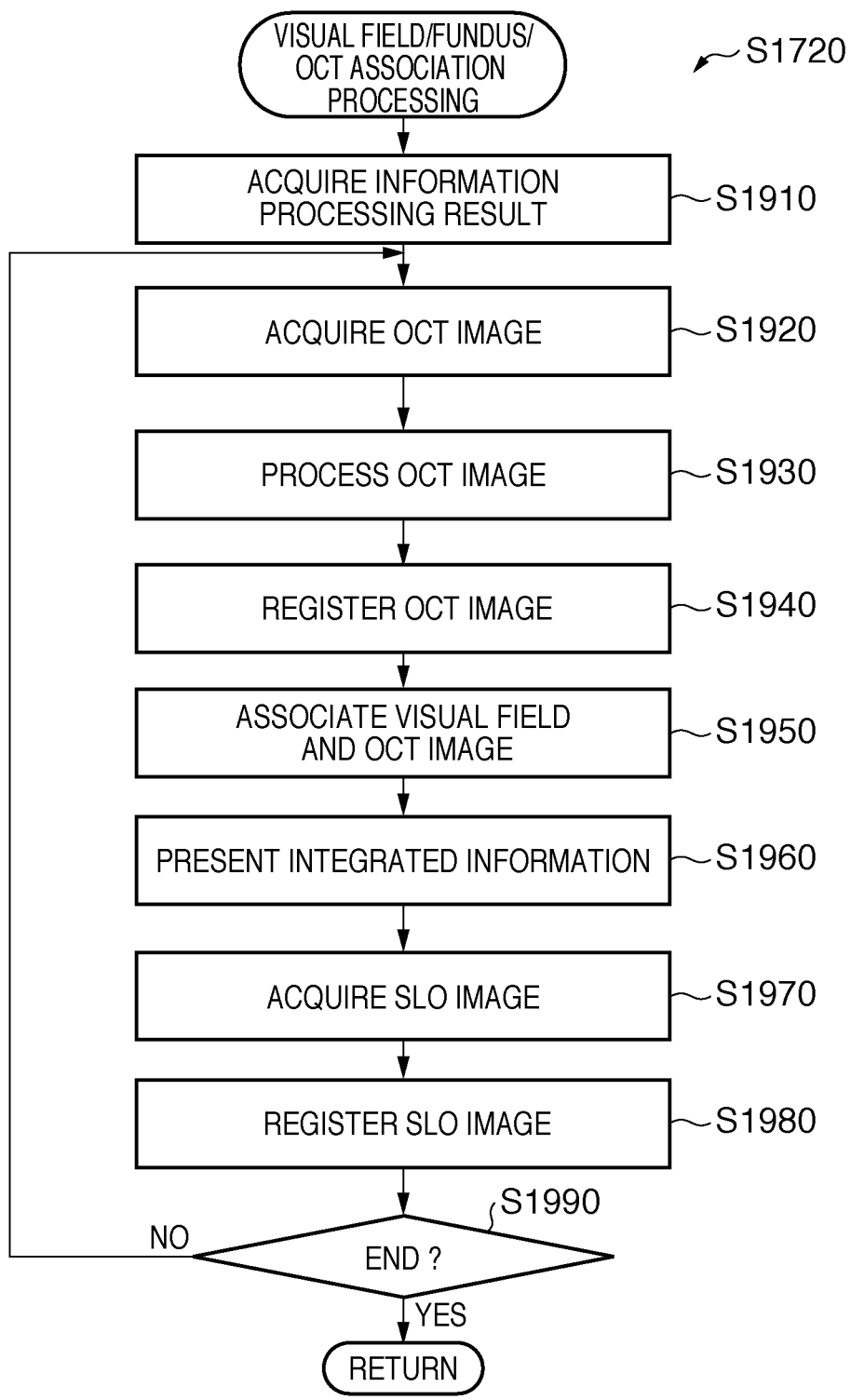
FIG. 19 is a flowchart showing visual field/fundus/OCT association processing according to the second embodiment.

The concrete contents of S1720 will be explained in detail with reference to the flowchart of FIG. 19. The information processing result acquiring unit 215 acquires associated information of a visual field sensitivity and layer thickness for each region that have been saved in the data server 40 in S480 and comprehensively analyzed for a case in the case database (S1910). The information processing result acquiring unit 215 transmits the acquired information to the storage unit 130.

The examined eye information acquiring unit 110 requests the examined eye information acquiring apparatus 20 to transmit an OCT image, and acquires the OCT image (S1920). The examined eye information acquiring unit 110 transmits the acquired information to the storage unit 130.

The registration unit 1660 acquires an OCT tomographic image from the storage unit 130, and extracts the nerve fiber layer from the tomographic image using the same method as that in S1330 (S1930). The registration unit 1660 registers the OCT image acquired in S1920 on the fundus camera image and visual field measurement results using the same method as that in S1340 (S1940).

The visual field/OCT associating unit 1670 associates the visual field sensitivity with the layer thickness of the nerve fiber layer using the fundus camera image, visual field measurement results, and OCT image which have been registered in S1940 (S1950). In this case, the same method as that in S450 is employed.

The integrated information presenting unit 1680 performs integrated information presentation processing (S1960). At this time, the integrated information presenting unit 1680 compares the visual field-layer thickness association result which has been obtained for the eye to be examined in S1950, with the integrated analysis result acquired in S1910. By using the same method as that in S1370, information is presented in a color explicitly indicating whether the relationship between the visual field and the layer thickness matches glaucoma. When there is a region considered not to suffer glaucoma, an alert is presented.

The examined eye information acquiring unit 110 requests the examined eye information acquiring apparatus 20 to transmit an SLO image, and acquires the transmitted SLO image (S1970). The examined eye information acquiring unit 110 transmits the acquired information to the storage unit 130.

The registration unit 1660 registers the integrated information presentation result obtained in S1960 on the SLO image saved in the storage unit 130 using the same method as that in S1840 (S1980). The registration unit 1660 transmits these results to the storage unit 130. In addition, the registration unit 1660 displays, via the display unit 140, the results of S1980 representing the relationship between the layer thickness and the visual field sensitivity on the SLO image.

The input result acquiring unit 120 acquires a result input by the operator, and determines whether to end the process (S1990). If it is determined in S1990 that there is no input to end the process, similar to S1850, the input result acquiring unit 120 determines not to end the process, and the process returns to S1970. Until the input result acquiring unit 120 receives an input to end the process or receives a result save instruction, the processing in S1720 continues to present the results of S1980 representing the relationship between the layer thickness and the visual field sensitivity on SLO images successively transmitted from the examined eye information acquiring apparatus 20.

According to the second embodiment, in OCT imaging, the OCT imaging region can be determined to image a region while confirming a region where the visual field is abnormal. It can be determined from the OCT imaging result whether the relationship between a change of the visual field sensitivity and a change of the layer thickness matches the glaucoma pattern. Based on the determination result, a region can be selected again and imaged by OCT.

Note that the functions of the information processing apparatus 10 and diagnosis support apparatus 15 in the above-described embodiments can be implemented by software in a computer.

Figure 20:
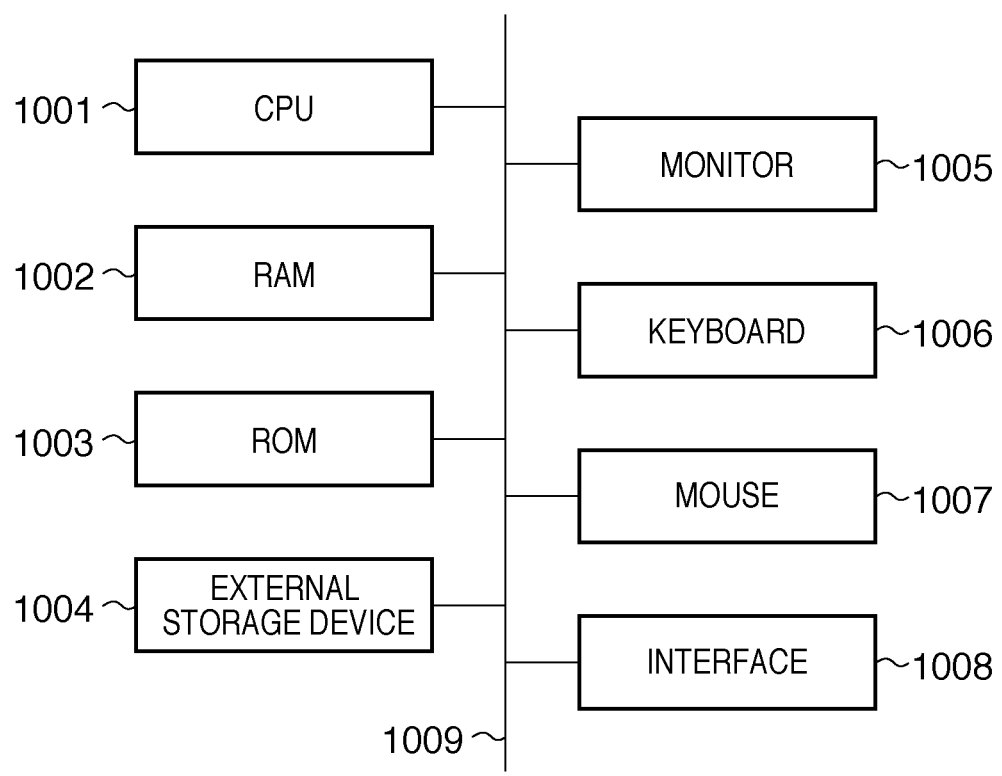
FIG. 20 is a block diagram exemplifying the arrangement of a computer for implementing the functions of the embodiment.

FIG. 20 is a block diagram showing the basic arrangement of a computer for implementing the respective units of the information processing apparatus 10 and diagnosis support apparatus 15 by software. A CPU 1001 controls the whole computer using programs and data stored in a RAM 1002 and ROM 1003. The CPU 1001 implements the functions of the respective units of the information processing apparatus 10 by controlling execution of software corresponding to the respective units.

The RAM 1002 has an area for temporarily storing programs and data loaded from an external storage device 1004, and a work area necessary to execute various processes by the CPU 1001. The RAM 1002 has the function of the storage unit 130.

The ROM 1003 generally stores the BIOS, setting data, and the like of a computer. The external storage device 1004 functions as a large-capacity storage device such as a hard disk drive, and saves an operating system, programs to be executed by the CPU 1001, and the like. Information which is known in the description of the embodiment is saved in the external storage device 1004 and if necessary, loaded to the RAM 1002.

A monitor 1005 is formed from a liquid crystal display or the like. The monitor 1005 can display, for example, contents output from the display unit 140. A keyboard 1006 and mouse 1007 are input devices. The operator can use the keyboard 1006 and mouse 1007 to give various instructions to the information processing apparatus 10. The functions of the examined eye information acquiring unit 110 and input result acquiring unit 120 are implemented via these input devices.

An interface 1008 is used to exchange a variety of data between the information processing apparatus 10 and an external device. The interface 1008 is formed from an IEEE1394 interface, USB, Ethernet® port, or the like. Data acquired via the interface 1008 is input to the RAM 1002. For example, the function of the result output unit 150 is provided via the interface 1008. These building elements are connected to each other via a bus 1009.

Other Embodiments

The present invention can also be achieved by executing the following processing. More specifically, software (program) for implementing the functions of the above-described embodiments is supplied to a system or apparatus via a network or various types of storage media. The computer (for example, a CPU or MPU) of the system or apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. A medical image processing apparatus comprising:
a processor; and
a memory storing instructions that, when executed by the processor, cause the apparatus to:
acquire a tomographic image of an eye to be examined;
acquire a result of a visual field measurement for the eye to be examined;
detect, from the tomographic image, a layer thickness of a predetermined layer of the eye to be examined;
display information indicating a relationship between the layer thickness and the result of the visual field measurement, wherein the information is displayed in a display form in accordance with the layer thickness and the result of the visual field measurement, the display form being changed in accordance with the layer thickness and the result of the visual field measurement;
acquire a fundus image of the eye to be examined;
associate the layer thickness and the result of the visual field measurement with the fundus image;
create a graph representing the relationship between the layer thickness and the result of the visual field measurement as the information based on the association; and
segment a region of the graph into a plurality of cells, wherein the relationship graph is displayed in different color gradations indicating a stage of glaucoma, and wherein a color gradation for each of the plurality of segmented cells is determined based on the relationship between the layer thickness and the result of the visual field measurement, and
wherein the relationship graph includes abscissa and ordinate axes, and one of the abscissa and the ordinate axes indicates the layer thickness and the other of the abscissa and ordinate axes indicates the result of the visual field measurement.

2. The apparatus according to claim 1, wherein the information is determined based on the relationship between a mean value of the layer thicknesses of the plurality of cells and a mean value of the results of the visual field measurements of the plurality of cells.

3. The apparatus according to claim 1, wherein the instructions further cause the apparatus to normalize the layer thickness in each of the plurality of cells, based on a reference value,
wherein the information is determined based on the relationships between the normalized layer thickness and the result of the visual field measurement for each of the plurality of cells.

4. The apparatus according to claim 3, wherein the reference value is a mean distribution value of a layer thickness in a normal case.

5. The apparatus according to claim 3, wherein normalization of the layer thickness excludes the layer thickness at a central pit from the normalization.

6. The apparatus according to claim 1, wherein the region is segmented with reference to a first straight line that connects a macula lutea and an optic disc of the fundus image and a second straight line that perpendicularly intersects the first straight line.

7. The apparatus according to claim 6, wherein the region is defined by a straight line parallel to the first straight line and a straight line parallel to the second straight line.

8. The apparatus according to claim 1,
wherein the point of intersection of the abscissa and the ordinate axes indicates the origin,
wherein on the axis indicating the layer thickness, the layer thickness increases depending on the distance from the origin, and
wherein on the axis indicating the result of the visual field measurement, visual field sensitivity value increases depending of the distance from the origin.

9. The apparatus according to claim 8,
wherein the relationship graph includes a measurement point indicating correspondence between the layer thickness and the result of the visual field measurement, and
wherein the instructions further cause the apparatus to determine a form of display of the measurement points, based on the distance from a predetermined point on the axis indicating the layer thickness to the measurement point, and the angle between a straight line that connects the predetermined point and the measurement point and the axis indicating the result of the visual field measurement.

10. The apparatus according to claim 1, wherein a cell determined to deviate from glaucoma based upon the relationship between the layer thickness and the result of the visual field measurement is displayed in a different color gradation from other cells.

11. The apparatus according to claim 1, wherein the predetermined layer is a nerve fiber layer in a retina layer.

12. The apparatus according to claim 1, wherein the instructions further cause the apparatus to:
acquire a projection image created by integrating pixel values of the acquired tomographic image in a depth direction, wherein the projection image is associated with the layer thickness; and
associate the result of the visual field measurement with the layer thickness by associating the result of the visual field with the fundus image and associating the projection image with the fundus image.

13. The apparatus according to claim 12, wherein the association of the result of the visual field measurement and the fundus image is based on the position of a macula lutea.

14. The apparatus according to claim 12, wherein the association of the projection image and the fundus image is based on images of blood vessels which are extracted from the projection image and the fundus image, respectively.

* * * * *